United States Patent [19]
Reichert et al.

[11] Patent Number: 5,037,399
[45] Date of Patent: Aug. 6, 1991

[54] APPARATUS FOR THE ADMINISTRATION OF MEDICATIONS TO ANIMALS

[76] Inventors: Elmer L. Reichert, 3980 W. 136th Ave.; David P. Sievers, 335 Dover Ct., both of Broomfield, Colo. 80020

[21] Appl. No.: 376,755

[22] Filed: Jul. 7, 1989

[51] Int. Cl.5 ..... A61M 5/178
[52] U.S. Cl. ..... 604/184; 604/223; 604/231
[58] Field of Search ..... 119/72, 72.5, 159, 160; 222/309; 604/54, 71, 73, 77, 121, 181, 183, 184, 186, 187, 207, 218, 223, 228, 231, 233, 236, 289, 290; 128/200.14

[56] References Cited

U.S. PATENT DOCUMENTS

| | | | |
|---|---|---|---|
| 1,995,971 | 3/1935 | Dowling | 604/231 |
| 2,168,493 | 8/1939 | Plews | 222/309 |
| 2,374,368 | 4/1945 | Mejia | 604/183 |
| 2,643,655 | 6/1953 | McKay | 604/184 |
| 3,527,386 | 10/1970 | Close et al. | 222/309 |
| 3,682,175 | 8/1972 | Halter | 604/223 |
| 3,901,402 | 8/1975 | Ayres | 604/218 |
| 4,020,838 | 5/1977 | Phillips et al. | 604/223 |
| 4,033,346 | 7/1977 | Phillips et al. | 604/223 |
| 4,073,293 | 2/1978 | Phillips et al. | 604/183 |
| 4,245,757 | 1/1981 | Phillips et al. | 222/309 |

FOREIGN PATENT DOCUMENTS

| | | | |
|---|---|---|---|
| 0102184 | of 0000 | Australia | 604/223 |
| 0014463 | 7/1929 | Australia | 604/223 |
| 0108012 | 7/1939 | Australia | 604/223 |

*Primary Examiner*—John D. Yasko
*Assistant Examiner*—Anthony Gutowski
*Attorney, Agent, or Firm*—Klaas & Law

[57] ABSTRACT

Apparatus for administering liquid medication to an animal is provided and includes an elongated administering rod having a first one way valve adjacent to the tip thereof and which rod is connected to a hollow housing in which there is located a barrel syringe so that measuring indicia thereon is visible, a hollow piston mounted for reciprocal movement in the barrel syringe, a closure member for holding the barrel syringe in place and through which a hollow piston rod having the piston attached thereto reciprocates. Apparatus is provided for reciprocating the piston rod and piston. A fitting is attached to the piston rod and is connected by a flexible tube to a supply of liquid medication and a second one way valve is mounted in the fitting. When the liquid medication is being administered, the first one way valve is open and the second one way valve is closed. When the liquid medication is being aspirated into the barrel syringe, the first one way valve is closed and the second one way valve is open.

8 Claims, 2 Drawing Sheets

APPARATUS FOR THE ADMINISTRATION OF MEDICATIONS TO ANIMALS

FIELD OF THE INVENTION

This invention relates generally to the field of the oral administration of liquid medications to animals and is particularly directed to the oral administration of relatively low volume, highly concentrated liquid medications to animals using a spray technique.

BACKGROUND OF THE INVENTION

There are presently on the market many differing types of apparatuses often called drenching guns or dose syringes for the oral administration of liquid medications to animals using a spray technique. A typical type of these apparatuses has an elongated rod which is placed in the mouth of the animal. The rod is connected to a barrel syringe which has a piston mounted therein. The piston is connected to a piston rod which is connected to operating means which is generally a spring urged trigger pivotally mounted on the handle so that the trigger is normally in the position to be pushed forward to apply the dosage. Adjusting means are provided to control the movement of the trigger to control the dosage. The piston rod is hollow and has one end connected to the piston and the other end connected to a supply of the liquid medication. At some place between the piston and the supply, a one way valve is used to control the flow of the liquid medication from the supply to the barrel syringe. When applying medication to a plurality of animals using the above-described existing apparatus, the elongated rod may be accidentally pointed downward so that a portion of the liquid medication in the elongated rod may drip therefrom. Since this liquid medication is very expensive, this is a problem to be concerned about. Also, the pivotal mounting of the trigger limits the distance that the piston rod and piston may be moved so that the barrel syringe needs to have a relatively large diameter which causes difficulty in setting the proper dosage to be applied. Thus, there existed a need for a new apparatus for the oral administration of low volume, highly concentrated liquid medications to animals.

BRIEF DESCRIPTION OF THE INVENTION

This invention provides apparatus for the oral administration of a relatively low volume, highly concentrated liquid medication to animals wherein there is substantially no dripping of the liquid medication out of the elongated administrating rod; the extent that the piston may be moved is increased so that a smaller diameter barrel syringe may be used so that more accurate dosages may be administered and the piston is manually movable so that the dosage amount may be readily changed.

In a preferred embodiment of the invention, the apparatus for the oral administration of a relatively low volume, highly concentrated liquid medication to animals comprises an elongated, hollow, angularly shaped administrating rod having one end thereof which is to be placed in the oral pharynx of the animal's mouth. A one way valve is located within a removable hollow cap which is removably threaded onto the one end of the administrating rod. The other end of the administrating rod is connected by a suitable fitting to the outlet of a barrel syringe. The barrel syringe preferably is of the disposable type marketed by Sherwood under the trade designation "Monoject" having a capacity of 12 cc. A hollow housing is provided for holding the barrel syringe and has an opening formed therein so that the dosage indicia on the barrel syringe may be readily observed. A hollow piston is secured to one end of a piston rod and is adapted to be placed within the barrel syringe with the other end of the piston rod extending through a closure member which is threadedly secured to the housing. The hollow piston has two O-rings and a cup ring mounted thereon. A handle member has one end thereof threadedly mounted on a stud which projects outwardly from the closure member. Moving means are provided for moving the piston rod to move the piston and comprises a plunger knob which is fixedly mounted on the piston spaced from the other end thereof and a trigger lever which has one end thereof rotatably mounted on one end of a first bar which has its other end rotatably mounted on the plunger rod. The other end of the trigger lever is rotatably mounted on one end of a second bar which has its other end fixedly mounted on the other end of the handle member. A hollow fitting is attached to the piston rod and has a one way valve located therein. A flexible tube extends between and is connected to the hollow fitting and a supply of the liquid medication.

In operation, the supply of liquid medication is contained in a plastic bottle which is mounted in a conventional shoulder harness with the cap side thereof at the lowermost location and which also has mounting means for holding the apparatus for the oral administration of the liquid medication and the plastic tube is attached to the plastic bottle by a hose barb secured on the plastic bottle cap. The apparatus is filled with the liquid medication by holding the elongated hollow administrating rod in an upright position in one hand while the other hand grasps the plunger knob and pulls back on it to start aspirating the liquid medication out of the plastic bottle. Air is eliminated from the system by operating the plunger knob to move the piston through the bottle syringe. Care should be exercised in removing the last remaining amount of air so that the amount of the liquid medication lost is held to a minimum and the piston rod is located as close as possible to the discharge end of the barrel syringe. The plunger knob is then grasped and pulled backwardly to position the piston opposite to the indicia on the barrel syringe that indicates the dosage of the liquid medication that is to be administered. The apparatus for administering the liquid medication is then placed in the shoulder harness. The animal patient, such as an equine patient, is then positioned by the operator who then removes the apparatus from the shoulder harness and positions the one end of the administrating rod at the proper location in the mouth of the animal and operates the trigger lever to move the piston toward the discharge end of the barrel syringe to eject the proper amount of the liquid medication out of the administrating rod into the animal patient's throat. The one way valve in the hollow fitting rod remains in a closed position during the administration of the liquid medication. The one way valve in the removable hollow cap is in the open position as the liquid medication is being administered but closes as soon as the movement of the piston is stopped so that substantially none of the liquid medication is lost as the administrating rod is removed from the animal patient's mouth. After the liquid medication has been administered, the plunger knob is grasped and pulled to move the piston in the opposite direction. During this movement, the one way valve in the removable hollow cap remains in the closed position while the one way valve in the hollow fitting opens so that liquid medication is aspirated into the barrel syringe. The movement of the piston is stopped when the piston is opposite to the indicia that indicates the dosage of the liquid medication that is to be administered. When the movement of the piston is stopped, the one way valve in the hollow fitting moves to the closed position.

BRIEF DESCRIPTION OF THE DRAWINGS

An illustrative and presently preferred embodiment of the invention is shown in the accompanying drawings in which.

DETAILED DESCRIPTION OF THE INVENTION

Figures 1, 1A, 1B, 1C, 2:
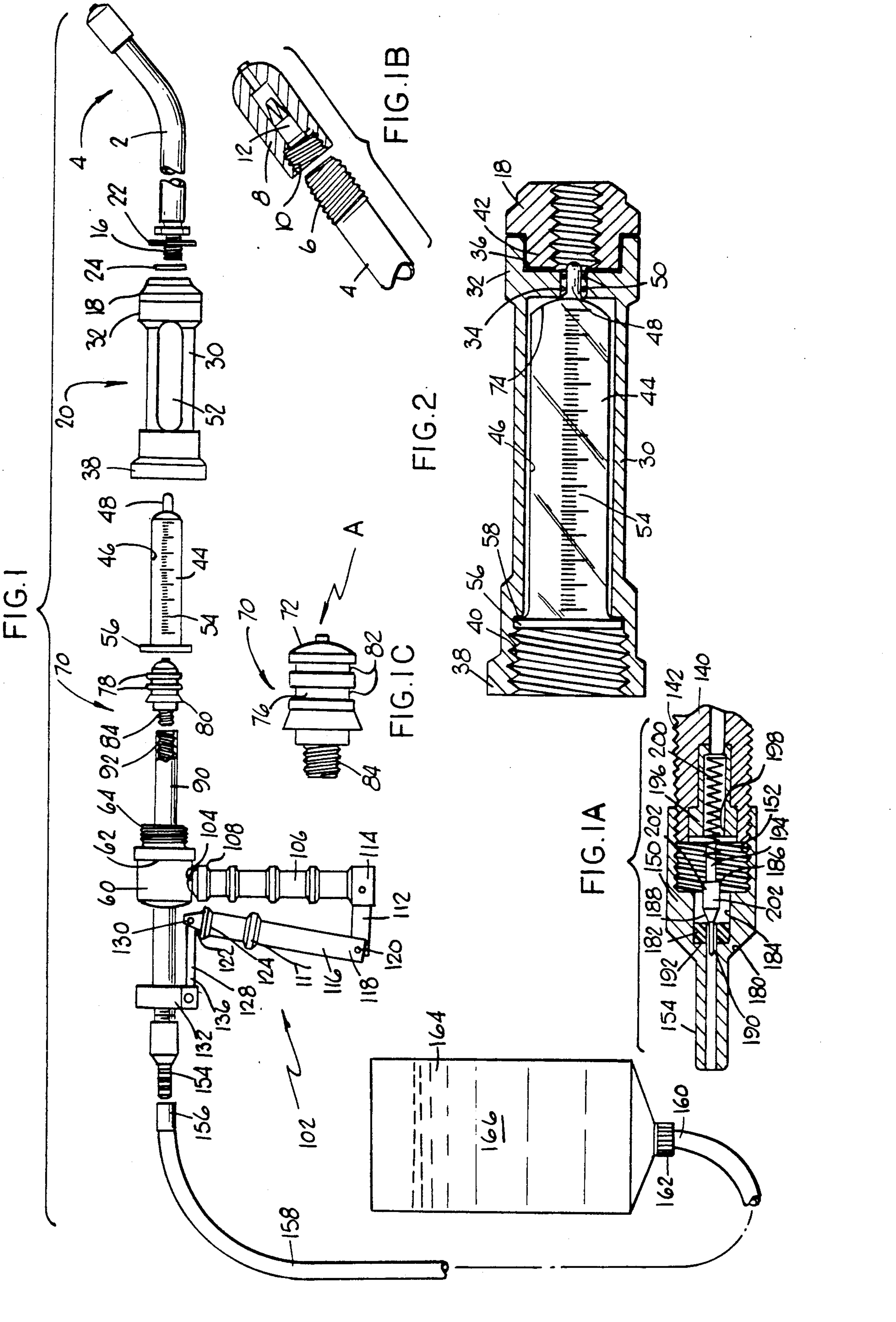
FIG. 1 is an exploded view illustrating the various components of the apparatus of this invention.
FIG. 1A is an enlarged view of a first portion of FIG. 1.
FIG. 1B is an enlarged view of a second portion of FIG. 1.
FIG. 1C is an enlarged view of a third portion of FIG. 1.
FIG. 2 is an enlarged view with parts in section of the mounting of the barrel syringe.
Figure 3:
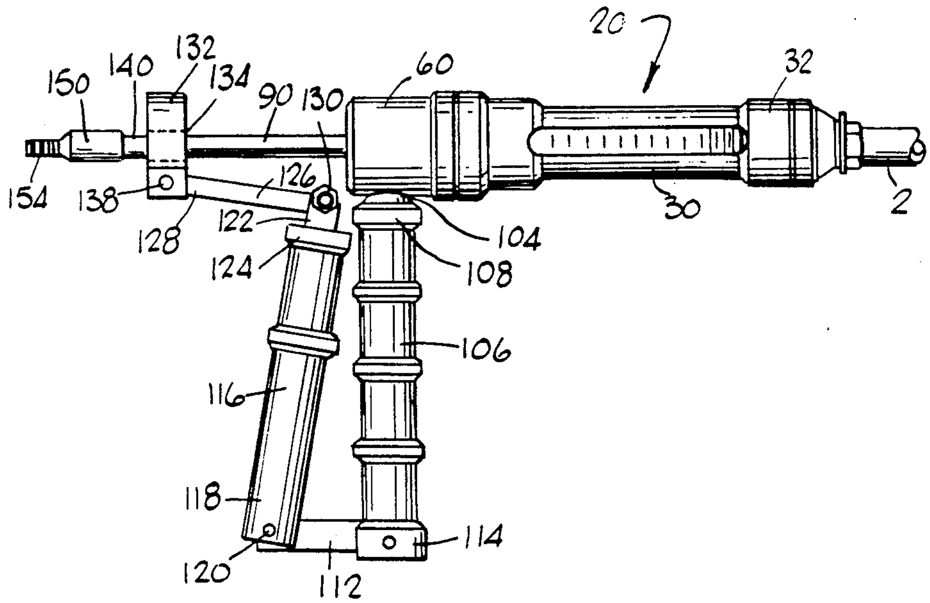
FIG. 3 is an enlarged view of a portion of the apparatus after the administration of a dosage of the liquid medication.

A preferred embodiment of the apparatus A of this invention is illustrated in FIG. 1 and comprises an elongated, hollow, angularly shaped administrating rod 2 having one end 4 having an externally threaded portion 6 and which is to be placed in the oral pharynx of the animal's mouth. A removable hollow cap 8 has an internally threaded portion 10 adapted to mate with the externally threaded portion 6. A one way valve 12, such as a rubber duck bill valve marketed by Vernay Lab under the trade designation Va 3143, is located in the hollow cap 8 and is held in place by the end of the administering rod 2 when the hollow cap 8 is threaded onto the administrating rod 2. The other end 14 of the administrating rod 2 has a threaded end 16 which is threadedly mounted in a fitting 18 press fitted into a hollow housing 20. A washer 22 and an O-ring 24 are used to provide a fluid tight connection between the other end 14 and the fitting 18.

The hollow housing 20, illustrated more specifically in FIG. 2, has a central body portion 30, a first end portion 32 having an opening 34 and another larger opening 36 and a second end portion 38 having an internally threaded portion 40. The fitting 18 has a projecting portion 42 which is press fitted into the larger opening 36. A hollow barrel syringe 44 having a generally cylindrical sidewall 46 and a tip portion 48 is inserted into the hollow housing 20 so that the tip portion 48 passes through the opening 34. A pair of O-ring sealing gaskets 50 mounted on the tip portion 48 and provide a liquid tight seal between the tip portion 48 and the opening 34. The central body portion 30 is provided with a viewing aperture 52 so that the dosage measuring indicia 54 may be readily observed when the barrel syringe 44 is within the hollow housing 20. The barrel syringe 44 has a flange portion 56 adapted to contact an internal shoulder portion 58 in the hollow housing 20 so that the barrel syringe 44 will be properly located in the hollow housing 20. A hollow closure member 60 having a central passageway 62 is provided for closing the hollow housing 20 and has an externally threaded portion 64 which is threadedly engaged with the internally threaded portion 40. The end of the externally threaded portion 64 contacts the flange portion 56 of the barrel syringe 48 to hold it firmly in place.

A piston 70 is provided for reciprocal sliding movement in the barrel syringe 44 and has a leading edge portion 72 which is shaped for mating engagement with the internal end surface 74 of the barrel syringe 44. The piston 70 has a central body portion 76 on which are mounted two rubber O-rings 78 and a rubber U-cup 80. The rubber O-rings 78 and U-cup 80 have outer diameters greater than the inner diameter of the sidewall of the barrel syringe 44 so as to have a friction fit therewith and to be in a sealing fluid tight engagement therewith. The rubber O-rings 78 and the U-cup 80 are mounted in grooves 82 on the central body portion 76 so as to prevent axial movement thereof. The inner diameters of the O-rings 78 and the U-cup 80 are smaller than the outer diameters of the grooves 82 so as to be in fluid tight relationship therewith. The piston 70 has an externally threaded end portion 84.

A hollow piston rod 90 passes through the passageway 62 in the closure member 60 and has one end portion 92 which is internally threaded so as to be threadedly engaged with the externally threaded end portion 84 of the piston 70. Conventional pipe sealing tape (not (shown) is used to form a fluid tight seal therebetween.

Figure 4:
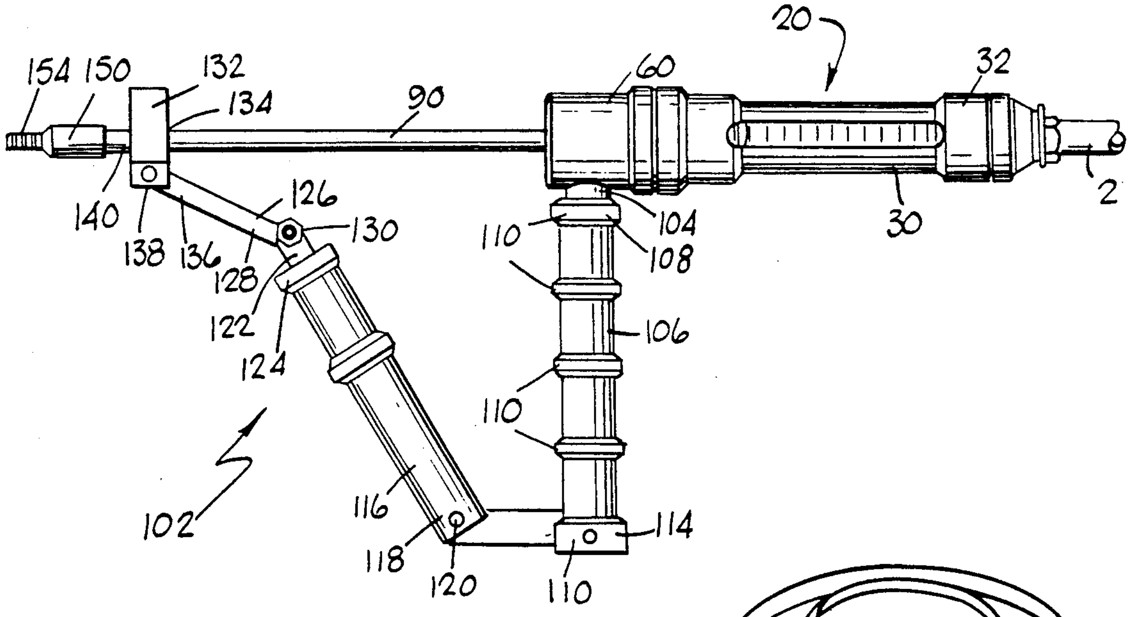
FIG. 4 is an enlarged view of a portion of the apparatus in position to administer a dosage of the liquid medication.

Moving means 102 are provided for providing the reciprocal sliding movement of the piston 70. An externally threaded stud 104 projects outwardly from the closure member 60. A handle member 106 has an internally threaded one end portion 108 so that the handle member 106 may be threadedly mounted on the stud 104. Flange portions 110, FIG. 4, are provided on the handle member 106 for providing spaces for the fingers of the operator to grasp the handle member 106. A support bar 112 is fixedly mounted in a slot (not shown) in the other end portion 114 of the handle member 106. A trigger lever 116 is pivotally connected at one end 118 by pivot means 120 to the support bar 112 and has a flange portion 117 to provide space for the juncture of the thumb and index finger. An extension member 122 projects outwardly from the other end 124 of the trigger lever 116 and is pivotally connected to one end 126 of a linkage lever 128 by pivot means 130. A plunger knob 132 has a central opening 134 so that it may be positioned on the piston rod 90. Suitable means, such as a set screw (not shown), are used to lock the plunger knob 132 on the piston rod 90. The other end 136 of the bar 128 is pivotally connected to the plunger knob 132 by pivot means 138. The above-described moving means 102 permits the piston rod 90 to be reciprocated in a linear path.

Figure 5:
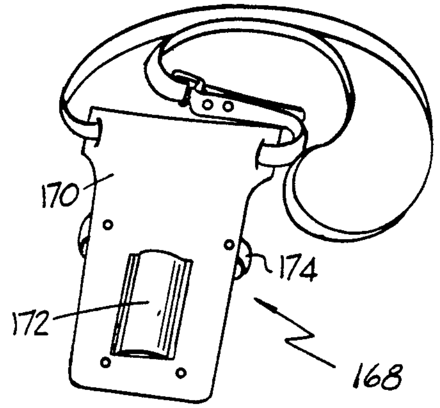
FIG. 5 is an illustration of the shoulder harness to be used with the apparatus of this invention.

The other end portion 140 has an externally threaded portion 142. A hollow fitting 150 has an internally threaded portion 152 adapted to mate with the externally threaded portion 142. The hollow fitting 150 has a hollow end portion 154 on which is sealingly mounted one end portion 156 of a flexible transparent plastic tube 158, FIG. 1. The other end portion 160 is secured to a cap 162 threaded onto a transparent plastic bottle 164 having a supply of liquid medication 166 therein so that when the plastic bottle 164 is inverted, the liquid medication 166 can flow through the plastic tube 158. Suitable means (not shown) are provided in the cap 162 so that the supply of liquid medication 166 is under atmospheric pressure. A shoulder harness 168, FIG. 5, is provided for supporting the apparatus A for administering the liquid medication 166 and the plastic bottle 164. The shoulder harness 168 comprises a base support 170 having an open ended pocket 172 for supporting the apparatus A and a strap 174 for supporting the plastic bottle 164.

A one way valve 180, such as that marketed by Tecumse under the trade designation 6309-32a, is located in the hollow fitting 150 and comprises a sealing ring 182 positioned in a passageway 184. A movable piston 186 has a tapered conical surface 188 which is adapted to be moved into or out of sealing engagement with the sealing ring 182. A leading portion 190 extends through an opening 192 in the sealing ring 182. A stem portion 194 projects rearwardly from the movable piston 186. A fitting 196 is located in the other end portion 140 of the piston rod 90 and has a central opening 198 in which is seated a resilient helical spring 200. When the fitting 150 is threaded onto the other end portion 140, the free end of the helical spring passes over the stem portion 194 and bears against the body portion 202 of the piston 186 to urge the tapered conical surface into sealing engagement with the sealing ring 182.

In operation, a supply of liquid medication 166 is contained in the plastic bottle 164 which is supported on a conventional shoulder harness 168 which also has an open ended pocket 172 for holding the apparatus A for the oral administration of the liquid medication and wherein the other end portion 160 is secured to the cap 162 and is in fluid communication with the interior of the plastic bottle 164 so that when the plastic bottle is secured to the shoulder harness 168 and is ready for use, the cap 162 is at a lowermost location so that the liquid medication will flow out of the plastic bottle 164 into the plastic tube 158. The apparatus A is filled with the liquid medication by holding the apparatus A with the removable cap 12 in an upright condition in one hand while the other hand grasps the plunger knob 132 and pulls back on it to start aspirating the liquid medication 166 out of the plastic bottle 164. Air is eliminated from the system by operating the plunger knob 132 to move the piston 70 through the bottle syringe. When the piston 70 is being moved toward the administrating rod 2, the one way valve 180 is in the closed position and the one way valve 12 opens to let the air out of the system. When the piston 70 is being moved in the opposite direction, the one way valve 12 is in the closed position and the one way valve 180 opens to allow the liquid medication to be aspirated into the system. Care should be exercised in removing the last remaining amount of air so that the amount of the liquid medication 166 lost is held to a minimum and the piston 70 is located as close as possible to the discharge end of the barrel syringe 48. The plunger knob 132 is then grasped and pulled backwardly to position the piston 70 opposite to the indicia 54 on the barrel syringe 48 that indicates the dosage of the liquid medication 166 that is to be administered. The apparatus A for administering the liquid medication is then placed in the shoulder harness 168. The animal patient, such as an equine patient, is then positioned by the operator who then removes the apparatus A from the shoulder harness 168 and positions the cap 12 on the one end 4 of the administrating rod 2 at the proper location in the mouth and operates the trigger lever 116 to move the piston 70 toward the discharge end of the barrel syringe 48 to eject the proper amount of the liquid medication out of the administrating rod 2 into the animal patient's throat. The one way valve 180 remains closed during the administration of the liquid medication 166. The one way valve 12 in the hollow removable cap is in the open position as the liquid medication 166 is being administered but closes as soon as the movement of the piston 70 is stopped so that substantially none of the liquid medication 166 is lost as the administrating rod is removed from the animal patient's mouth. After the liquid medication 166 has been administered, the plunger knob 136 is grasped and pulled to move the piston 70 in the opposite direction. During this movement, the one way valve 12 remains in the closed position while the one way valve 180 opens so that liquid medication 166 is aspirated into the barrel syringe 48. The movement of the piston 70 is stopped when the piston 70 is opposite to the indicia 54 that indicates the dosage of the liquid medication 166 that is to be administered. When the movement of the piston 70 is stopped, the one way valve 180 moves to the closed position.

The "Monojet" barrel syringe 48 used in this application is a disposable syringe many of which are normally carried by a veterinarian so that, if something happens to the barrel syringe in the housing, it may be readily replaced.

While an illustrative and presently preferred embodiment of the invention has been described in detail herein, it is to be understood that the inventive concepts may be otherwise variously embodied and employed and that the appended claims are intended to be construed to include such variations except insofar as limited by the prior art.

What is claimed is:

1. Apparatus for the oral administration of liquid medication to an animal comprising:
   - an elongated hollow administrating rod having opposite end portions, one end portion serving as a discharge end portion and the other end portion serving as the inlet end portion;
   - a first one way valve mounted in said elongated hollow administrating rod for permitting liquid flow from within said administrating rod into said animal but preventing liquid flow in the opposite direction;
   - a barrel syringe having at least one discharge end portion;
   - a holding means with a hollow housing for holding said barrel syringe;
   - connecting means for connecting the other of said opposite end portions of said elongated hollow administrating rod to said at least one discharge end portion in a fluid tight relationship;
   - a hollow piston mounted for reciprocal movement in said barrel syringe;
   - a hollow piston rod having opposite end portions with one of said opposite end portions connected to said piston so that movement of said hollow piston rod moves said hollow piston;
   - moving means for applying reciprocating movement to said piston rod;
   - container means for holding a supply of said liquid medication;

liquid conducting means for conducting portions of said liquid medication from said supply of liquid medication to the other of said opposite end portions of said hollow piston rod;

a second one way valve for permitting liquid flow from said supply of liquid medication to said piston rod but preventing liquid flow in the opposite direction;

an elongated handle grip having opposite end portions with one of said opposite end portions secured to said holding means and located so as to extend generally downwardly from said holding means when in use;

a support bar fixedly mounted on the other of said opposite end portions of said handle grip and extending outwardly therefrom generally in a horizontal direction when in use;

a plunger knob secured to said piston rod adjacent to said other of said opposite end portions of said piston rod thereof;

a lever having a central body portion and opposite end portions;

pivot means for pivotally connecting one of said opposite end portions of said lever and said plunger knob;

a trigger lever having a central body portion and opposite end portions;

pivot means for pivotally connecting the other of said opposite end portions of said lever and one of said opposite end portions of said trigger lever; and pivot means for pivotally connecting the other of said opposite end portions of said trigger lever and said support bar.

2. Apparatus as in claim 1 and further comprising:

said discharge end portion of said elongated hollow administrating rod having an externally threaded portion;

a hollow cap;

said first one way valve mounted in said hollow cap; and said hollow cap having an internally threaded portion for engagement with said externally threaded portion of said discharge end portion.

3. Apparatus as in claim 1 and further comprising:

the other of said opposite end portions of said piston rod having an externally threaded portion;

a hollow fitting connecting said liquid conducting means to said other of said opposite ends of said piston rod for permitting liquid flow therebetween;

said second one way valve being located in said hollow fitting; and said hollow fitting having an internally threaded portion for engagement with said externally threaded portion of said piston rod.

4. Apparatus as in claim 2 and further comprising:

the other of said opposite end portions of said piston rod having an externally threaded portion;

a hollow fitting connecting said liquid conducting means to said other of said opposite ends of said piston rod for permitting liquid flow therebetween;

said second one way valve being located in said hollow fitting; and said hollow fitting having an internally threaded portion for engagement with said externally threaded portion of said piston rod.

5. Apparatus as in claim 1 wherein said piston comprises:

a hollow central body portion having an outer peripheral surface; and sealing means mounted on said central body portion in frictional engagement with said barrel syringe for providing a liquid tight seal between said barrel syringe and said piston but permitting said reciprocal movement of said piston.

6. Apparatus as in claim 5 and further comprising:

measuring indicia on said barrel syringe;

said hollow housing having an opening formed therein; and said barrel syringe being located in said hollow housing so that said measuring indicia is visible through said opening.

7. Apparatus as in claim 6 wherein said holding means comprises:

a closure member having said central passageway extending therethrough;

said closure member having an externally threaded portion;

a flange on said barrel syringe; and an internal shoulder in said hollow housing so that when said externally threaded portion on said closure member is threaded into said internally threaded portion of said hollow housing and tightened, said flange will be clamped against said internal shoulder and said closure member.

8. Apparatus as in claim 6 and further comprising:

said one of said opposite end portion of said piston rod having an internally threaded portion; and said piston having an externally threaded portion adapted to mate with said internally threaded portion of said piston rod so that said hollow piston may be removably secured on said piston rod.

* * * * *